(12) United States Patent
Brown et al.

(10) Patent No.: US 6,514,258 B1
(45) Date of Patent: Feb. 4, 2003

(54) PENETRATION LIMITING STOP ELEMENTS FOR A DRILL BIT USED FOR BONE TISSUE

(75) Inventors: William G. Brown, West Palm Beach, FL (US); Ralph E. Goodman, West Palm Beach, FL (US)

(73) Assignee: Implant Innovations, Inc., Palm Beach Gardens, FL (US)

( * ) Notice: Subject to any disclaimer, the term of this patent is extended or adjusted under 35 U.S.C. 154(b) by 0 days.

(21) Appl. No.: 09/374,189

(22) Filed: Aug. 13, 1999

Related U.S. Application Data

(60) Provisional application No. 60/107,024, filed on Nov. 4, 1998.

(51) Int. Cl.[7] ............................................. A61B 17/16
(52) U.S. Cl. ........................ 606/80; 606/172; 408/202; 408/203; 408/41 S
(58) Field of Search ............................... 606/79, 80, 86, 606/180, 172; 433/72, 102, 165, 166, 180, 172; 408/202, 203, 41 S

(56) References Cited

U.S. PATENT DOCUMENTS

| | | | |
|---|---|---|---|
| 74,466 A | * | 2/1868 | Whiting |
| 2,353,514 A | * | 7/1944 | Slater |
| 2,700,905 A | * | 2/1955 | Urquhart |
| 3,000,239 A | * | 9/1961 | Ransom |
| 4,123,193 A | * | 10/1978 | Hill |
| 4,710,075 A | * | 12/1987 | Davison |
| 5,078,552 A | * | 1/1992 | Albel |
| 5,078,605 A | | 1/1992 | Sutter et al. |
| 5,429,504 A | | 7/1995 | Peltier et al. |
| 5,569,035 A | | 10/1996 | Balfour et al. |
| 5,741,267 A | | 4/1998 | Jorneus et al. |
| 5,785,522 A | | 7/1998 | Bergstrom et al. |
| 5,791,902 A | | 8/1998 | Lauks |
| 6,162,226 A | * | 12/2000 | DeCarlo, Jr. et al. |

FOREIGN PATENT DOCUMENTS

| | | |
|---|---|---|
| DE | 91 06 606 | 9/1992 |
| EP | 0 454 639 A1 | 3/1991 |
| EP | 0 682 917 A1 | 4/1995 |
| EP | 0 799 605 A2 | 10/1997 |
| WO | WO 98/03119 | 1/1998 |

OTHER PUBLICATIONS

Friatec "Price List" (Oct. 1998).
Friatec "Friatec®–2, Abridged Directions For Use" (date believed to be prior to filing date of present application).
Frialet®–2, "OP–Tray Surgical Tray," set of 8 pictures (date believed to be prior to filing date of present application).
3i Implant Innovations, *Surgical Catalog*, Oct. 1996 (50 pp.).
3i Implant Innovations, *Surgical Catalog*, Oct. 1997 (102 pp.).

* cited by examiner

*Primary Examiner*—Michael H. Thaler
(74) *Attorney, Agent, or Firm*—Jenkens & Gilchrist

(57) ABSTRACT

The stop element is set forth for solving a problem of the clinician only being able to visualize a depth marking on a drill bit or a similar tool. The detachable stop element limits the penetration of the drill bit beyond a predetermined axial distance on the drill bit. The stop element consists of a connecting portion and an extending portion, both having an inner wall defining a bore extending entirely through the connecting portion and extending portions. The connecting portion has a surface that contacts the drill bit for restricting the axial movement of the stop element relative to the drill bit. The extending portion terminates in a lower end for engaging the bone surrounding the bore to limit the penetration of the drill bit. The stop element may include a plurality of grooves for altering its length so that the penetration depth of the drill bit can be altered.

40 Claims, 8 Drawing Sheets

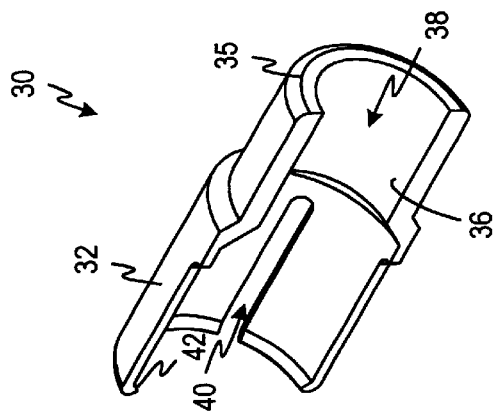
FIG. 7
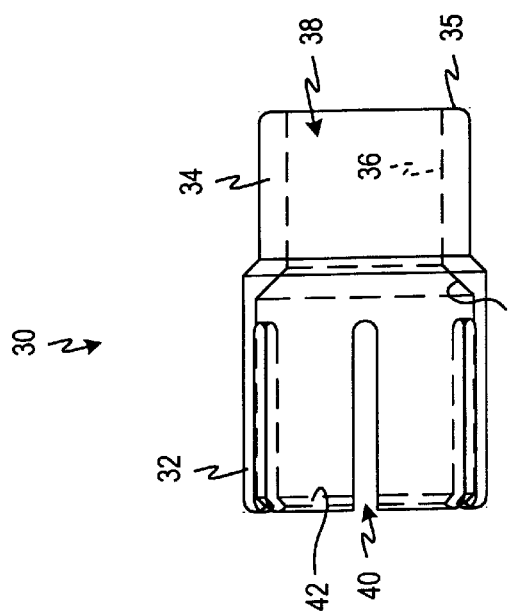
FIG. 4
FIG. 5
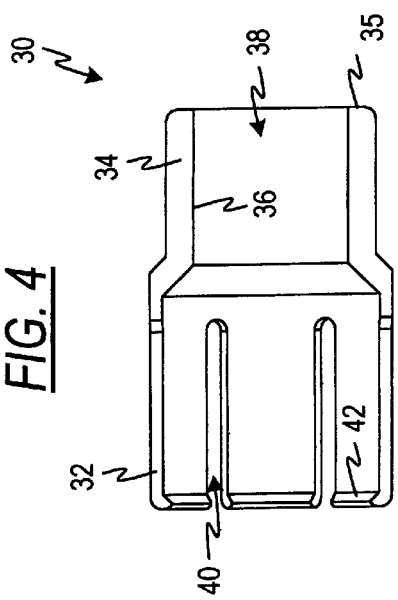
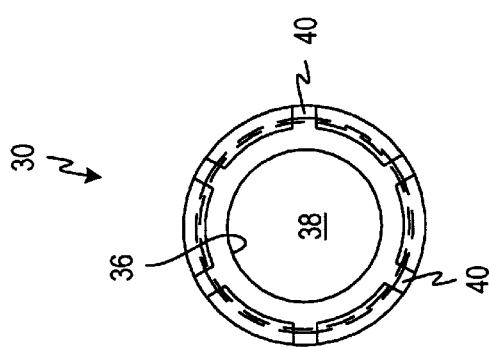
FIG. 6

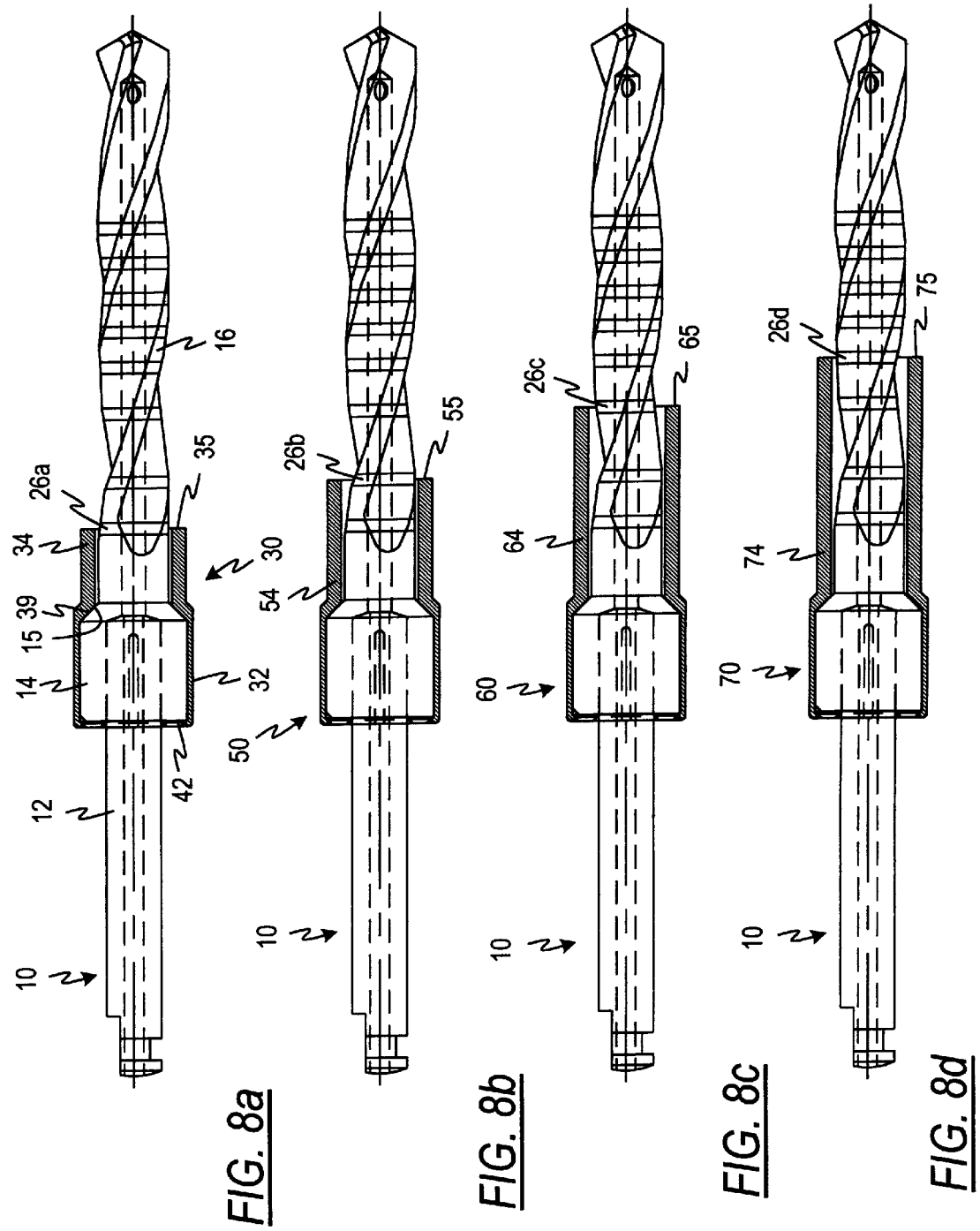

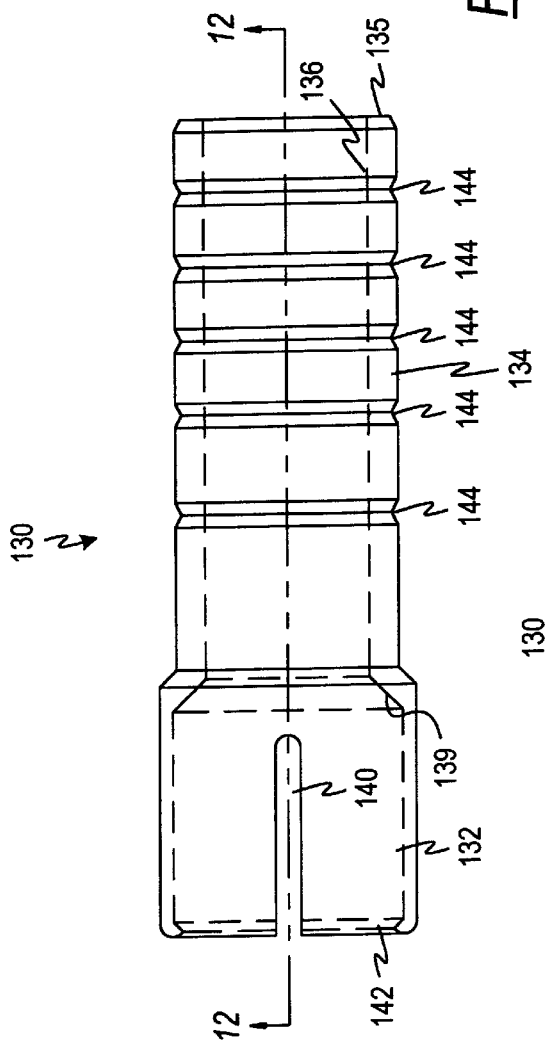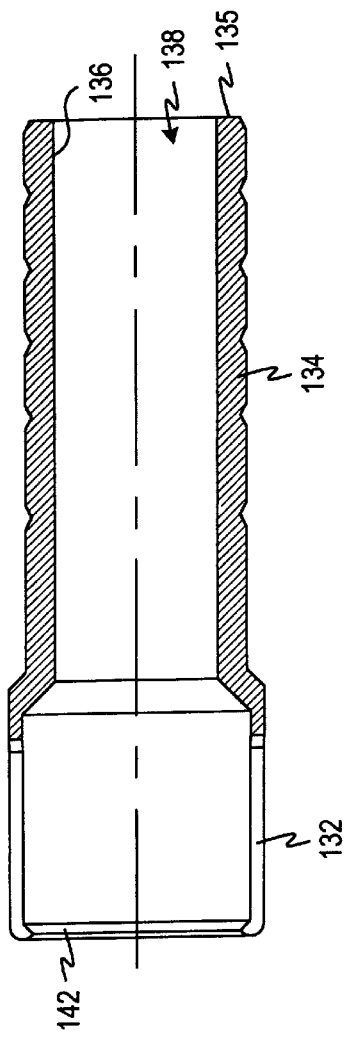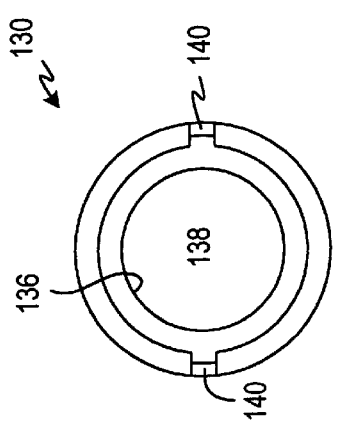

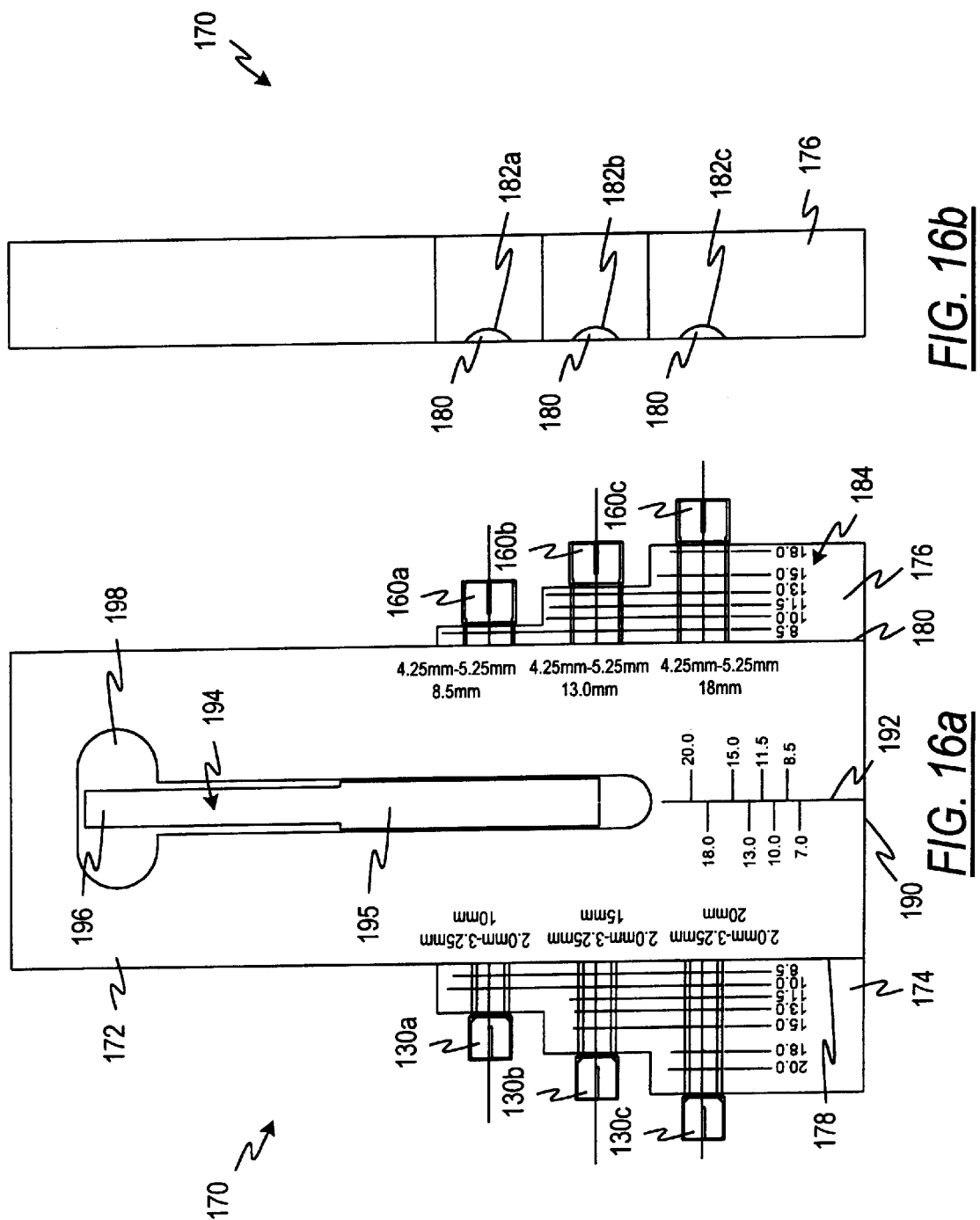

PENETRATION LIMITING STOP ELEMENTS FOR A DRILL BIT USED FOR BONE TISSUE

CROSS-REFERENCES TO RELATED APPLICATIONS

This is a complete application claiming priority to co-pending provisional U.S. patent application Ser. No. 60/107,024 filed on Nov. 4, 1998.

FIELD OF THE INVENTION

This invention relates to devices for developing a bore in bone tissue and, in particular, to a novel stop element that prohibits insertion of that device into the bone tissue beyond a predetermined depth.

BACKGROUND OF THE INVENTION

It is common for a dentist to use tools, such as drills, to create bores in bone tissue of a patient's mouth. Drills come in various styles, sizes and lengths but all have a common goal of creating a bore of a known size. The diameter of the drill dictates the diameter of the bore. However, the length of the bore is determined by the amount of axial movement that the clinician imparts on the drill as he or she inserts it into the bone tissue.

The size of the bore created by the clinician is a critical parameter in the restoration of the dentition of the patient's mouth. For example, if the length of the bore is too long, it can puncture the sinus cavity if it is placed in the maxillary, or the mandibular canal which contains nerves if it is placed in the mandible. Likewise, the roots of adjacent teeth also can be affected by the size of the bore.

To ensure that the drill bit is inserted into the bone to a known length, the drill bit often contains several markings on it which signify specific depths. For example, a drill bit may have a marking on it that, when located at the surface of the bone, indicates the bore depth is 10 mm. The use of these visual markers is, of course, limited to the clinician's ability to see the mark as the drill is being inserted into the patient's mouth. Accordingly, the clinician is required to keep his or her eye on the depth marker as he or she slowly proceeds with the axial movement that causes the drill bit to be inserted deeper and deeper into the bone.

SUMMARY OF THE INVENTION

The present invention solves the problem related to the clinician only being able to visualize a depth marking. A detachable stop element is provided that limits the penetration of the drill bit beyond a predetermined axial distance. The drill stop according to the present invention consists of a connecting portion and an extending portion, both having an inner wall defining a bore extending entirely therethrough. The drill bit is inserted through the bore. The connecting portion has a surface that contacts the drill bit for restricting the axial movement of the drill stop relative to the drill bit. The extending portion terminates in a lower end for engaging the bone surrounding the bore to limit the penetration of the drill bit.

With the drill stop surrounding the drill bit, the lower end of the drill stop is positioned adjacent to the drill bit at a predetermined length from the distal end of the drill bit. Accordingly, the clinician is restricted from creating a bore that is longer than the predetermined length since the lower end engages the upper surface of the bone around which the bore is being created.

The drill stop can be made of a frangible material such that it can be served at various positions along that extending portion.

BRIEF DESCRIPTION OF THE DRAWINGS

In the accompanying drawings:

FIG. 4 is a side view of a drill stop according to the present invention;

FIG. 5 is a cross-sectional side view of the drill stop of FIG. 4;

FIG. 6 is an end view of the drill stop of FIG. 4;

FIG. 7 is an isometric cross-sectional view of the drill stop of FIG. 4;

FIGS. 8A–8D are assembly drawings of drill stops of various lengths on the drill bit of FIG. 1;

FIG. 11 is side view of a polymeric drill stop according to the present invention capable of having several lengths due to break its grooves;

FIG. 12 is a cross-sectional side view of the drill stop of FIG. 11;

FIG. 13 is an end view of the drill stop of FIG. 11;

FIG. 16 illustrates a cutting the polymeric drill stops of FIGS. 11–15.

DETAILED DESCRIPTION OF THE DRAWINGS

Figure 1:
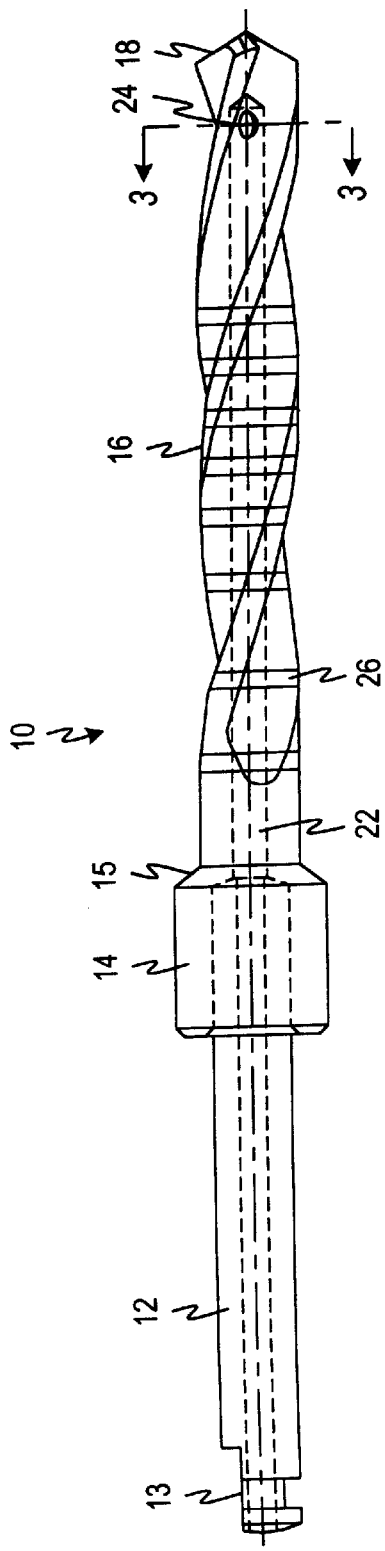
FIG. 1 is a side view of a drill bit for a bone.

FIG. 1 illustrate a typical drill bit 10 used for developing a bore in bone tissue, such as in the jawbone. The drill bit 10 includes a drive shank 12 at its one end which terminates in a drive attachment 13. The drive attachment 13 is configured to mate with a corresponding dental drill, or like device, which imparts rotating motion to the drill bit 10.

The drive shank 12 is connected to a collar 14 which turn is connected to a plurality of flutes 16. The collar 14 includes a tapered region 15 where it transitions from its larger diameter to the smaller diameter of the flutes 16. Each of the flutes 16 terminates in a cutting edge 18 which slices the bone tissue to develop the bore. The number of flutes 16 in the drill bit 10 of FIG. 1 is three, but the number can vary.

Because of the mechanical energy that is converted to heat along the flutes 16 and especially at the cutting edges 18, the drill bit 10 includes an irrigation channel 22 which extends along its length to a point near the cutting edges 18. As seen best in FIG. 3, the irrigation channel 22 terminates in a plurality of openings 24. Accordingly, biocompatible fluid id transported through the irrigation channel 22 and released into the bore via the openings 24 to reduce the friction between the rotating drill bit 10 and the bore tissue and inhibit a temperature increases which may harm the bone tissue. As shown,the irrigation channel extends through the drive attachment 13.

The drill bit 10 is of stainless steel although other materials are possible. While the drill bit 10 may be made of one integral piece of material, the drive shank 12 can be made a separate component from the combination of the collar 14 and flutes 16. In this situation, the drive shank 12 would be attached to the collar 14 through mechanical means, such as a press fit engagement.

As is known in the art, the drill bit 10 also includes a plurality of depth markings 26. Each marking 26 signifies a known distance from the cutting edges 18. The clinician drilling the bore uses these depth markings 26 to determine when the bore has been drilled to the proper depth. Of course, the clinician's ability to drill the bore to the desired depth is limited by his or her eyesight, and his or her line of sight to the bone to be drilled. Thus, drilling can be difficult when to bore is to be placed in the mandible or maxillary because the clinician is the required to perform the drilling procedure in the patient's mouth.

A drill stop 30 of the present invention is illustrated in FIGS. 4–7. The drill stop 30 includes a connecting portion 32 and extending portion 34 which terminates in a lower end 35. The drill stop 30 further includes an inner wall 36 which defines a bore 38 that extends entirely through the drill stop 30. The inner wall 36 has a tapered section 39 at the point where it transition from the extending portion 34 into the conecting portion 32.

The conecting portion 32 includes a plurality of slots 40 positioned therein. The plurality slots 40 create in the connecting portion 32 plurality of individual fingers which provide flexibility to the connecting portion 32. This flexibility, and its utility, will be described more with reference to FIGS. 8A–8D. The connecting portion 32 also has at its terminal end a catch element 42 which, in essence, is an inwardly tapering surface of the inner wall 36. The drill stop 30 can be made of various rigid materials such as metal or plastic.

Figure 2:
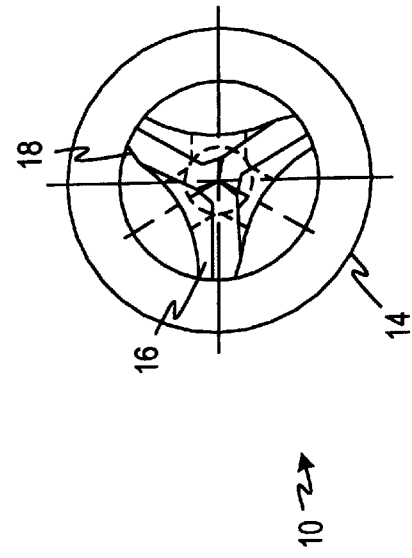
FIG. 2 is an end view of the cutting edges of the drill bit in FIG. 1.
Figure 3:
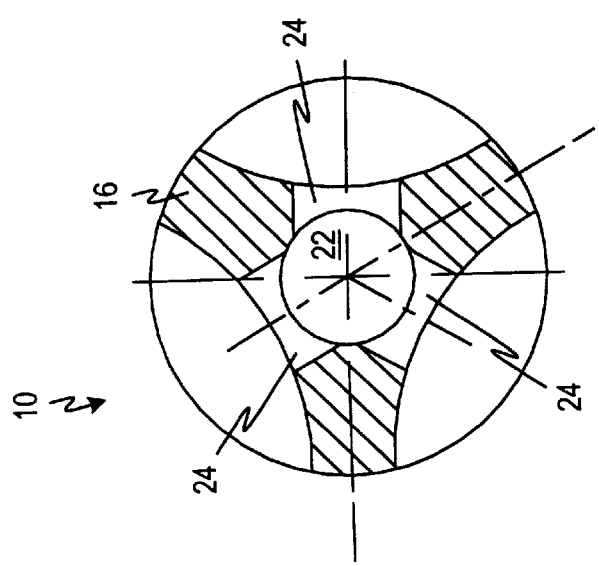
FIG. 3 is a cross-sectional view taken through 3—3 in FIG. 1.

In FIG. 8A the drill stop 30 is illustrated in use with the drill bit 10 shown in FIGS. 1–3. To assemble the pieces, the drill stop 30 is slid over the flutes 16 of the drill bit 10 such that the tapered section 39 of the inner wall 36 of the drill stop 30 contacts the tapered region 15 of the collar 14. During this assembly step, the connecting portion 32 of the drill stop 30 flexes outwardly while the drill stop 30 is being placed over the collar 14 of the drill bit 10. This flexibility, as mentioned previously, is brought about through the existence of the slots 40 as shown in FIGS. 4–7. Additionally, the catch elements 42 snap over the end of the collar 14 adjacent to the drive shank 12. Once the catch elements 42 snap over the collar 14, the axial movement of the drill stop 30 relative to the drill bit 10 is limited since the catch elements 42 limit movement of the drill stop 30 to the right (with respect to FIG. 8A), while the engagement of the tapered region 15 with the tapered section 39 limits the movement of the drill stop 30 to the left (with respect to FIG. 8A). To ensure that the axial movement of the drill stop 30 is limited in its operational position, the length of the connecting portion 32 is chosen to be the length of the collar 14.

The length of the extending portion 34 of the drill stop 30 is chosen to correspond with the length between the tapered region 15 and the depth marking 26a. In use, as the drill bit 10 rotates under the motion imparted to it by the driver, the clinician is then limited to inserting the drill bit 10 into the bone to any point beyond the lower end 35 of the drill stop 30 since it engages the upper surface of the bone around which the bore is being created. In other words, instead of the clinician relying solely on his or her ability to see the depth marker 26a and its relative position to the upper surface of the bone, the clinician now has the ability to feel the correct insertion depth as the lower end 35 of the drill stop 30 engages the upper surface of the bone.

Because the depth at which the bore is to be made depends on the prevailing conditions of the patient, the present invention contemplates providing a set of drill stops that limit the penetration of the drill bit into the bone to specific, predetermined lengths. As shown in FIG. 8B, a drill stop 50 includes an extending portion 54 which terminates in a lower end 55 corresponding to depth mark 26b on the drill bit 10. Likewise in FIG. 8C, a drill stop 60 includes an extending portion 64 which terminates at a lower end 65 corresponding to depth marking 26c. Lastly, a drill stop 70 in FIG. 8D includes an extending portion 74 with the lower end 75 terminating at depth marking 26d. Of course, the set of drill stops may also include drill stops which would correspond to the remaining four depth markings 26 located on drill bit 10.

While FIGS. 4–8 describe one basic embodiment of the drill stop 30, other configurations are also possible. For example, it might be beneficial to have a radially-extending flange at the lower end 35 (as shown in FIG. 8A) to provide for a larger surface for engaging the surface of the bone around which the bore is to be developed. Additionally, the connecting portion 32 may include a structure on its outer surface which allows the clinician to easily remove the drill stop 30 from the drill bit once it has been placed in its final position as shown in FIG. 8A. For example, the connecting portion 32 may include radially projections adjacent to the catch elements 42 on at least a few of the fingers created by the slots 40 to allow the clinician to push downwardly and cause radially outward motion of those fingers thereby releasing the catch elements 42 from the terminal end of the collar 14. Alternatively, the connecting portion 32 may have at its terminal end adjacent to the catch elements 42 a tapered surface which meets with the surface defining the catch elements 42. A tool with a corresponding annular tapered end could be slid over the drive shank 12 of the drill bit 10 thereby engaging these tapered surfaces to force the flexible connecting portion 32 outwardly and move the drill stop 30 from its operational position toward the flutes 16.

It should also be noted that if the drill bits and drill stops are sold as sets, then it is possible to remove the depth markings 26 from the drill bit 10 such that the clinician relies only upon the drill stop 30 for a determination of the depth at which the drill bit 10 is to be inserted, and not the depth marking 26. However, it may be beneficial to retain the existing depth markings 26 on the drill bit 10 because the clinician then has some assurance that the appropriate drill stop has been chosen that corresponds to a depth indicated by the depth markings 26 on the drill bit. In other words, this invention comtemplates using the set of drill stops on drill bits which contain or do not contain depth markings.

Furthermore, while the invention has been described with reference to drill bits, osteotome tools which create bores by the compaction of the bone tissue through the gradual increase in diameter of the osteotome tool can also benefit from the use of a stop element such as the drill stop 30. Thus, the drill stop 30 could be inserted over an osteotome tool to limit its insertion depth into the bone. Furthermore, bores in the bone may also need to be internally threaded through the use of a bone tap. These drill stops are equally useful on bone taps.

Figure 10:
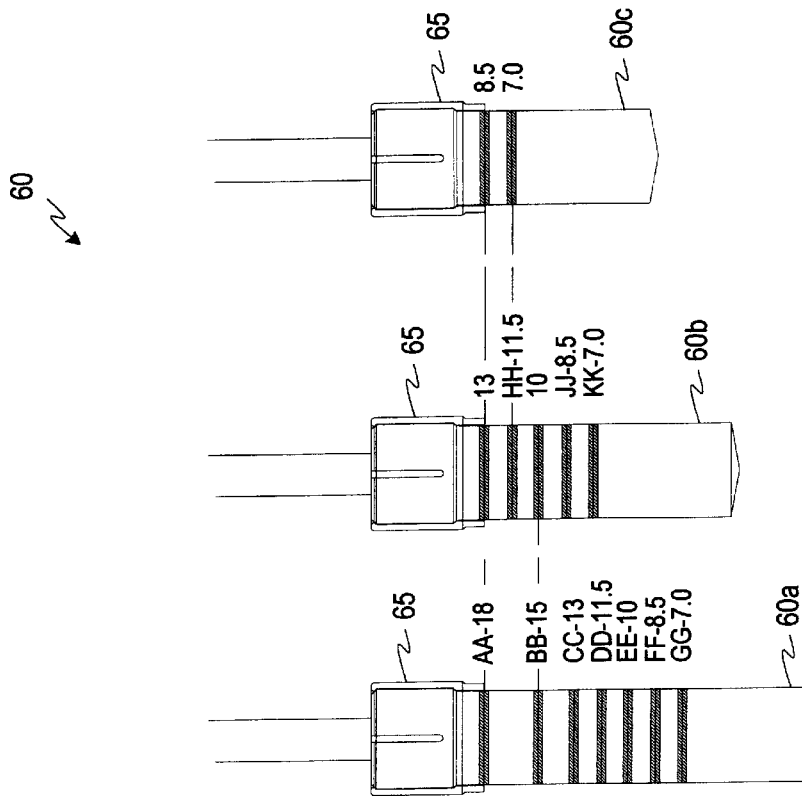
FIGS. 9–10 are schematic views of sets of drill bits in use with drill stops of the present invention.
Figure 9:
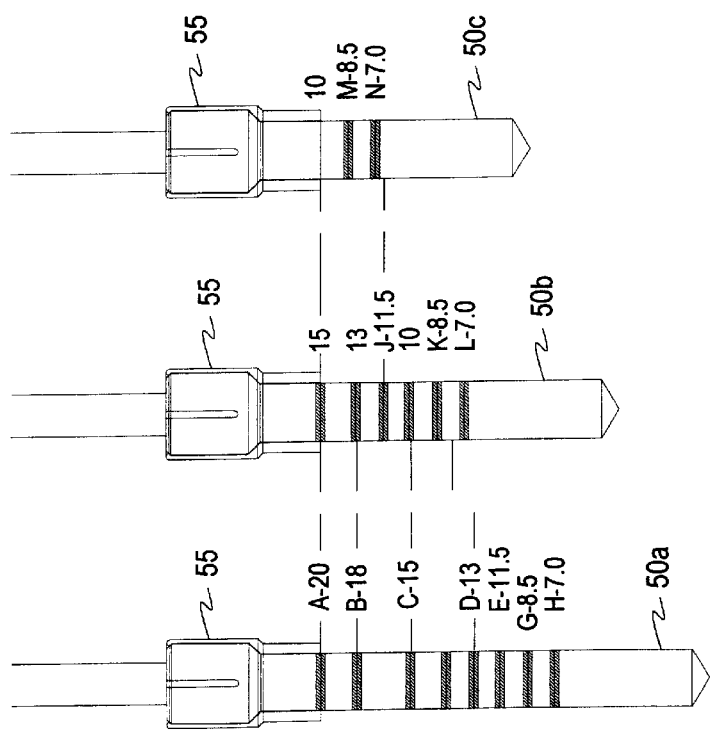

Referring now to FIGS. 9–10, a first diameter drill bit set 50 and a second diameter drill bit set 60 are illustrated respectively. In FIG. 9, the first diameter drill bit set 50 has three drill bits, 50a, 50b, and 50c, with three lengths. In FIG. 10, the second diameter drill bit set 60 also has three drill bits, 60a, 60b, and 60c. The collar size for each of the drill bits in the first diameter drill bit set 50 is the same regardless of its length. The same is true for the second diameter drill bit set 60 in FIG. 10. Accordingly, in FIG. 9, the same drill stop 55 can be used on each of the drill bits 50a, 50b, and 50c of the first diameter drill bit set 50. Likewise, the drill stop 65 can be used on each of the drill bits 60a, 60b, and 60c of the second diameter drill bit set 60.

Referring specifically to FIG. 9, drill bit 50a is a 20 mm length drill bit. Drill bit 50b is a 15 mm length drill bit. Drill bit 50c is a 10 mm length drill bit. Prior to the introduction of the novel drill stops of the present invention, the clinician would be required to line up the uppermost depth markings of drill bits 50a, 50b, and 50c (i.e. 20 mm, 15 mm, and 10 mm, respectively) with the surface of the bone to ensure the depth of the bore was accurately created at 20 mm, 15 mm, 10 mm, respectively. Now with the introduction of the drill stop 55, the clinician can feel when the appropriate depth has been reached due to the engagement of the lower end of the drill stop 55 with the bone tissue.

Furthermore, when looking specifically at drill bits 50a and 50b of FIG. 9, if the extending portion of the drill stop 55 were to extend downwardly for another 5 mm, the lower end of drill stop 55 would be at the length corresponding to the 15 mm depth marking on drill bit 50a, while at the 10 mm depth marking on drill bit 50b. In other words, the same drill stop (or drill stops) can be used on drill bits of various lengths to provide a positive stop at various insertion depths.

However, for simplicity, it may be most desirable to develop a set of drill stops associated for each drill bit. For example, a set of drill stops associated with drill bit 50a may be manufactured with a marking on it indicating that it is to be used only on drill bit 50a. The same would also be true for each of the drill bits 50b and 50c. Such a marking on the drill stops may be in the form of a labeling of the drill bit length or in the form of a color code. In other words, the drill stops to be used for drill bit 50a may be created in a blue color; the drill stops to be used for drill bit 50b may be created in a red color; and the drill stops for drill bit 50c may be created in a green color. It may further be possible to place the resulting length for each drill bit on each drill stop if that stop were to be used. For example, the drill stops in the set corresponding to drill bit 50a (which may be colored blue) may have on them a statement such as "L=20 mm," "L=18 mm," "L=15 mm," etc., so that the clinician knows the resulting length of the drill bit 50a when that stop is placed thereon.

While the collar sizes on the first diameter drill bit set 50 of FIG. 9 and the second diameter drill bit set 60 of FIG. 10 are shown to be different, drill bits for both diameter sizes could be made such that their collars are the same diameter and length. Thus, the same drill stop that is used for a 10 mm length drill bit with the 5 mm flute diameter could be used also for the 10 mm drill bit which has a 4 mm flute diameter. The primarily difference in the resulting assemblies is the gap size between the inner wall 36 within the extending portion 34 and the surface of the flutes 16 (as shown in FIG. 8A). Regardless of the gap size produced by the assemblies of the same drill stop on two drill bits of different diameters, the functionality would still be the same as its lower end would still engage the surface of the bone tissue adjacent to the bore that is being developed.

FIGS. 11–13 illustrate and alternate embodiment of the present invention in which a disposable drill stop 130 is constructed from a frangible material such as a polymeric material like polyethylene or polyoxymethylene (i.e. Delrin™). Although it was suggested with respect to the embodiment of FIGS. 4–7 that, for simplicity, it may be most desirable to develop a set of drill stops associated for each drill bit, the invention of FIGS. 11–13 reduces the number of drill stops required per drill bit since one drill stop 130 can be altered to accommodate each length associated with each depth marking of a specific drill bit.

As shown in FIGS. 11–13, the drill stop 130 includes a connecting portion 132 and an extending portion 134 terminating in a lower end 135. The drill stop 130 further includes an inner wall 136 that defines a bore 138 that extends entirely through the drill stop 130. The inner wall 136 has a tapered section 139 at the point where it transitions from the extending portion 134 into the connecting portion 132. The connecting portion 132 includes a plurality of slots 140 positioned therein. The plurality slots 140 create in the connecting portion 132 a plurality of individual fingers, which provide flexibility to the connecting portion 132. The connecting portion 132 also has at its terminal end a catch element 142, which, in essence, is an inwardly tapering surface of the inner wall 136.

Severing the drill stop 130 at one of the break grooves 144 varies the length of the extending portion 134 of the drill stop 130. The grooves 144 may extend entirely around the exterior of the extending portion 134 or around a part of it. The groves 144 preferably have a V-shaped cross-section. The break grooves 144 and the lower and 135 of drill stop 130 are arranged at locations which correspond with depth markings of a particular drill bit (or bits). The length of the extending portion 134 of the drill stop 130 is chosen to correspond with the length between the tapered region 15 and the lowermost depth marking. Another way to think of drill stop 130 is that is capable of having multiple lower ends that could ultimately engage the bone. When the drill stop 130 is severed, the part of the extending portion 134 adjacent to the severed groove 144 becomes the new "lower end."

Figure 14:
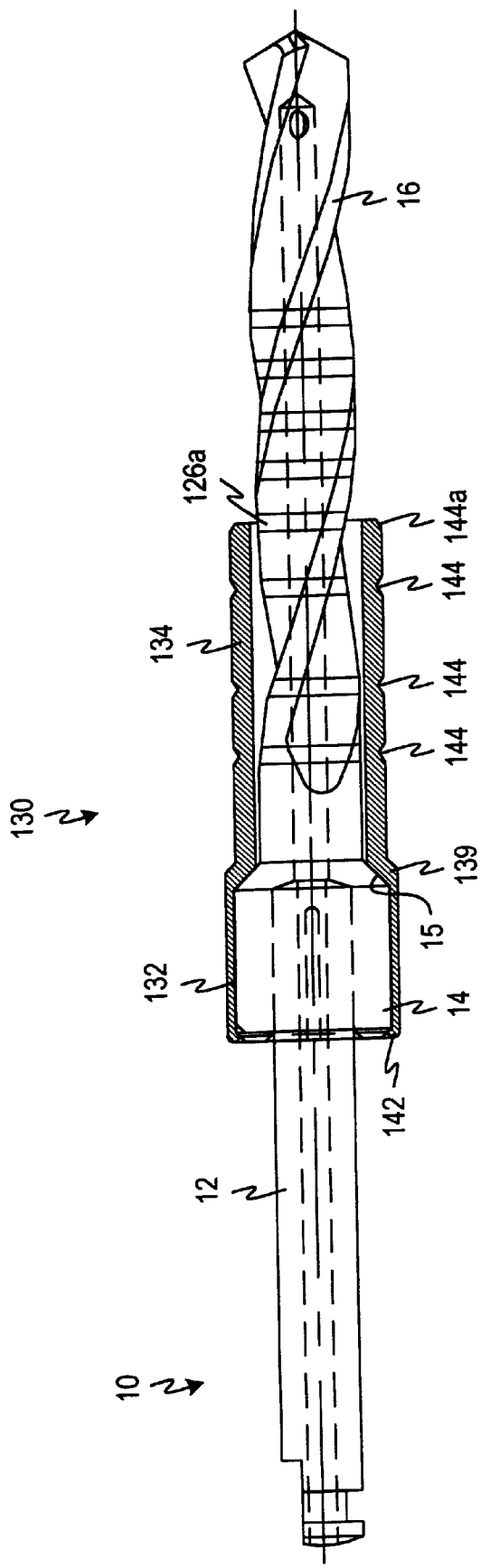
FIG. 14 is a side view of the drill stop of FIG. 11 attached to a drill bit.

In FIG. 14, the drill stop 130 is illustrated in use with the drill bit 10 shown in FIGS. 1–3. The drill stop 130 is assembled on the drill bit 10 in the same manner described above with reference to the drill stop 30 of FIGS. 4–8 after the drill stop 130 is severed at the break groove 144a corresponding to the desired depth marking 126a. Once the catch elements 142 snap over the collar 14, the axial movement of the drill stop 130 relative to the drill bit 10 is limited. Accordingly, the clinician is restricted from inserting the drill bit 10 into the bone beyond the break groove 144a (and the depth marking 126a) in the same manner described above with reference to the drill stop 30 of FIG. 8A.

The present invention comtemplates providing one drill stop 130 for each drill bit to limit the penetration of the drill bit into the bone to specific, predetermined lengths. The same drill stop 130 can be configured on one drill bit 10 to provide a positive stop at each insertion depth marking by severing the drill stop 130 at any one of the break groves 144 or leaving the drill stop intact. Accordingly, the clinician has a choice of multiple predetermined lengths for the drill stop 130 for use with the drill bit 10. Because drill bits of various flute diameters may have the same collar diameter and the drill stop 130 is designed to be coupled to the collar, the same drill stop can be used on drill bits of the same length, but of different flute diameters.

Alternatively, one drill stop may be created that has grooves corresponding to each depth marking on each drill bit having a particular collar size. Thus, one drill stop could be used for numerous drill bits of different lengths and different flute diameters.

Each drill stop 130 may also be created with a particular color to code it for a particular drill bit (or bits). It may further be possible to place a marking of the resulting insertion depths at the break grooves. For example, the drill stop 130 corresponding to drill bit 10 (which may be the color blue) may have on its exterior surface statements such as "L=20 mm," "L=18 mm," "L=15 mm," adjacent to the break grooves 144, so that the clinician knows the resulting insertion depth of the drill bit 10 when that drill stop 130 is severed at a specific one of the break grooves 144.

Figure 15:
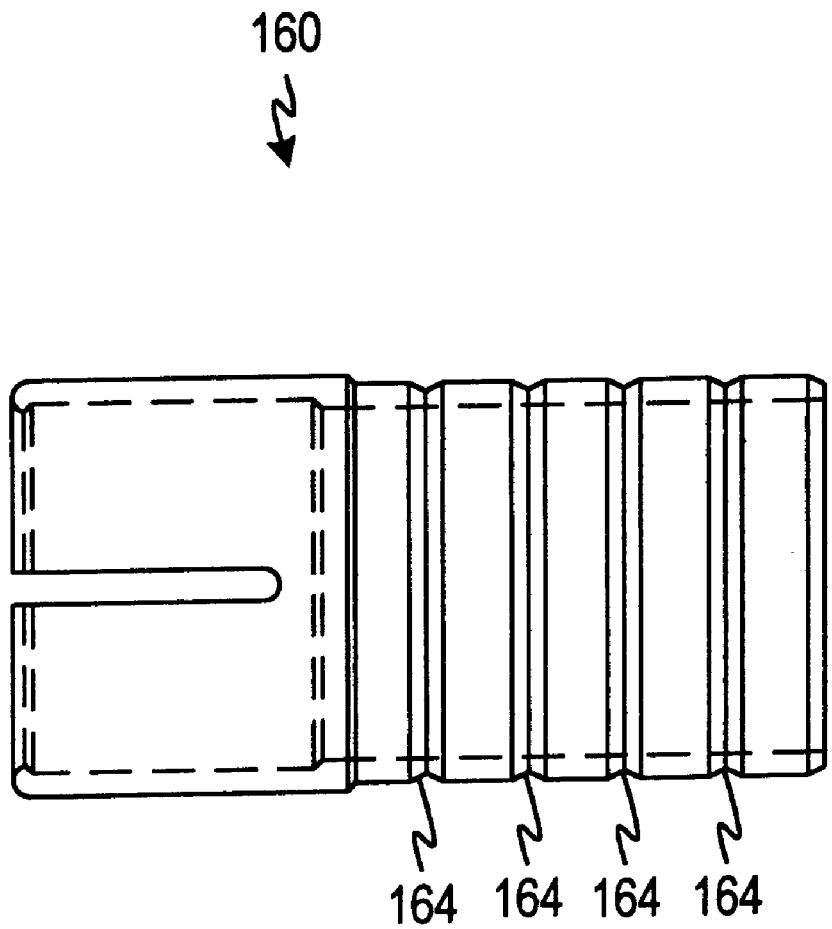
FIG. 15 illustrates an alternative polymeric drill stop of a different length and for a drill bit with a different collar diameter than the drill bit illustrated in FIG. 14.

FIG. 15 illustrates an alternate polymeric drill stop 160. The drill stop 160, in comparison with the drill stop 130 of FIGS. 11–14, is used on a drill bit having a larger collar. As mentioned previously, the collar diameter of two drill bits may be the same although the drill bits have a different flute diameter (e.g. 3.25 mm and 2.0 mm). However, drill bits with larger flute diameters usually have larger collars. Accordingly, the drill stop 160 of FIG. 15 is useful for a drill bit with a larger flute diameter than the drill stop 130 of FIGS. 11–14.

FIGS. 16a and 16b illustrate a cutting block 170 that is useful for severing the drill stops 130 and 160 at one of their break grooves 144. The cutting block 170 includes a main body 172 and first and second cutting regions 174 and 176, respectively. The first cutting region 174 meets the main body 172 at a first end surface 178. Likewise, the second cutting region 176 meets the main body 172 at a second end surface 182.

As shown best in FIG. 16b, the second cutting region 176 has three grooves 182a, 182b, and 182c. The grooves 182 have a diameter that is approximately the same as the diameter of the extending portion of drill stop 160 such that the drill stop 160 fits within the groove 182. When placed properly in the groove 182, the end of the drill stop 160 abuts against the second end surface 180. As such, the break grooves 164 (see FIG. 15) of the drill stop 160 are aligned with corresponding length markings 184 (e.g. 8.5 mm, 10.0 mm, 11.5 mm, 13.0 mm, 15.0 mm and 18.0 mm) on the second cutting region 176.

The clinician then takes a cutting instrument, such as an Exacto knife, and cuts the drill stop 160 to the correct length at the break groove 164 corresponding to the desired length marking 184. Of course, grooves are configured in the first cutting region 174 to accommodate three lengths of the drill stop 130.

The main body 172 also has a portion in its lower region adjacent to the lowermost end 190 that includes a final measuring scale 192 to ensure an accurate cut has been made. After cutting a drill stop to the appropriate length, the scale 192 allows the clinician to measure the length of available drill bit extending below the drill stop by placing the lower end of the drill stop against the lowermost end 190 of the body 172. Accordingly, the dental clinician will know the exact length of the drill bit that is available for insertion into the bone.

Furthermore, to assist the clinician in holding the drill stops 160a–160c, 130a–130c during the cutting process, a drill stop holder 194 is provided. The drill stop holder 194 has a larger end 195 and a smaller end 196. The smaller and 196 is capable of being received within the connecting portion of the drill stop 130 and the larger end 195 is capable of being received within the connecting portion of the drill stop 160. The stop holder 194 is placed within a recess 198 located within the main body 172. The recess 198 may include internal structure to allow the stop holder 194 to be press fit into the recess 198.

During the cutting process, the clinician holds the drill stop 130 against the first end surface 178 by exerting force on the stop holder 194 in a direction which pushes the lower end of the drill stop 130 but against the first end surface 178. Likewise, the clinician uses the stop holder 194 to hold the drill stop 160 against the second end surface 180. As such, the clinician does not have to rely upon using his or her fingers to hold the drill stop 160 steady as he or she cuts it.

The embodiment of FIGS. 11–16 will now be described with reference to one exemplary drill bit set. In a typical drill set for an entire product line of dental implants, a supplier may have, for example, drill bits with flute diameters of 2.00 mm, 2.75 mm, 3.00 mm, 3.15 mm, 3.25 mm, 4.25 mm and 5.25 mm. All drill bits with flute diameters in the range from 2.00 mm to 3.25 mm will have the same collar size. Likewise, the drill bits with the flute diameter of 4.25 mm and 5.25 mm will have the same collar size. Each flute diameter (e.g. seven of them) may also be made in three lengths leading to a total of 21 different drill bits. Thus, the entire set of drill bits will require only six drill stops (130a–130c, 160a–160c) to accommodate its entire line of drill bits.

As previously mentioned, osteotome tools which create bores by the compaction of the bone tissue through the gradual increase in diameter of the osteotome tool can also find benefit in the use of a stop element such as the drill stop 130. Furthermore, these drill stops are equally useful on bone taps.

While the present invention has been described with reference to one or more preferred embodiments, those skilled in the art will recognize that many changes may be made thereto without departing from the spirit and scope of the present invention as set forth in the appended claims.

What is claimed is:

1. A stop element for use with a tool having a working portion that assists in creating a bore in living bone, comprising:
   a generally tubular main body for surrounding said tool, said main body including a connecting portion with a structure for affixing said stop element relative to said tool, said connecting portion includes a plurality of distinct sections, adjacent ones of said plurality of distinct sections are separated by slots for providing flexibility to said connecting portion, said main body further including an extending portion for fitting over said working portion of said tool, said extending portion being positioned at a known and fixed position along said working portion of said tool when said stop element engages said bone and including a plurality of grooves for severing said extending portion at predetermined lengths.

2. The stop element of claim 1, wherein said tool includes a collar above a region that creates said bore, said connecting portion fitting over said collar.

3. The stop element of claim 2, wherein said connecting portion is dimensioned for fitting snugly over said collar.

4. The stop element of claim 2, wherein said connecting portion includes a tapering internal surface at each of its end regions, said tapering internal surfaces for engaging said collar.

5. The stop element of claim 4, wherein said connecting portion has interior surfaces defining an opening through which said tool is inserted, one of said interior surfaces being generally cylindrical with a diameter that is substantially the same as a transverse dimension of said collar, said one of said interior surfaces being positioned between said tapering internal surfaces.

6. The stop element of claim 4, wherein said affixing structure is one of said tapering surfaces.

7. The stop element of claim 1, wherein each of said plurality of grooves are for alignment with an insertion depth marking on said working portion of said tool.

8. The stop element of claim 1, wherein each of said plurality of grooves extends entirely around an exterior surface of said extending portion.

9. The stop element of claim 1, wherein each of said plurality of grooves has a V-shape when viewed in cross-section.

10. The stop element of claim 1, wherein said main body is constructed of a polymeric material.

11. A combination of a set of drill bits for creating a bore in living bone and a drill stop for use with each drill bit of said set, said set of drill bits including drill bits having various flute diameters, said drill stop being generally tubular and including a structure for affixing said drill stop relative to each of said drill bits, said drill stop having an extending portion with an internal wall defining an opening into which said selected one of said drill bits is inserted, said opening being of a size to receive each drill bit of said set having said various flute diameters, said internal wall terminating at a lower end of said extending portion for defining an insertion depth of a selected one of said drill bits, wherein said extending portion includes a plurality of grooves for severing said extending portion to reduce a length of said extending portion, each of said plurality of grooves being aligned with an insertion depth marking on said selected one of said drill bits, a part of said extending portion adjacent to a selected one of said plurality of grooves being said lower end for defining said insertion depth in response to said extending portion being severed at said selected one of said plurality of grooves.

12. The combination of claim 11, wherein said drill stop is constructed of a polymeric material.

13. The combination of claim 11, wherein said drill stop includes a connecting portion, said connecting portion including said affixing structure.

14. The combination of claim 13, wherein each of said set of drill bits includes a collar above a working portion that creates said bore, said connecting portion fitting over said collar.

15. The combination of claim 14, wherein said connecting portion is dimensioned to snugly fit over said collar.

16. The combination of claim 13, wherein said connecting portion includes a generally tapering surface at each of its end regions, said tapering surfaces for engaging said collar.

17. The combination of claim 16, wherein said affixing structure is one of said tapering surfaces.

18. The combination of claim 13, wherein said connecting portion includes a plurality of distinct sections, adjacent ones of said plurality of distinct sections are separated by slots for providing flexibility to said connecting portion.

19. A combination of a set of drill bits for creating a bore in living bone and a drill stop for use with each of said set of drill bits, said set of drill bits including drill bits having flutes of various lengths, said drill stop being generally tubular and including a structure for affixing said drill stop relative to each of said drill bits, said drill stop having an internal wall defining an opening into which said selected one of said drill bits is inserted, said internal wall terminating at a lower end for defining an insertion depth of a selected one of said drill bits.

20. The combination of claim 19, wherein each of said plurality of grooves is aligned with an insertion depth marking on said selected one of said drill bits.

21. The combination of claim 19, wherein said drill stop is constructed of a polymeric material.

22. The combination of claim 19, wherein said drill stop includes a connecting portion, each of said set of drill bits includes a collar above a working portion that creates said bore, said connecting portion fitting over said collar.

23. The combination of claim 19, wherein said lower end is aligned with a first depth marking on a first drill bit when said drill stop is affixed to said first drill bit, said lower end is aligned with a second depth marking on a second drill bit when said drill stop is affixed to said second drill bit, said first depth marking representing a different insertion depth than said second depth marking.

24. A kit for limiting the penetration depth of a tool that assists in creating a bore in living bone, said kit comprising:
at least one stop element for use with said tool, said stop element being generally tubular and including a structure for affixing said stop element relative to said tool, said stop element having an internal wall defining an opening into which said tool is inserted and an exterior wall terminating in a lower end, said exterior wall including a plurality of indicia representing known distances from said lower end; and
a cutting block for holding said stop element steady while said stop element is manually cut at one of said plurality of indicia.

25. The kit of claim 24, wherein said cutting block includes a reference surface against which said lower end is placed during cutting, said cutting block including depth lines located at known distances from said reference surface.

26. The kit of claim 25, wherein said depth lines are aligned with corresponding ones of said plurality of indicia when said lower surface is against said reference surface of said cutting block.

27. The kit of claim 24, wherein said cutting block includes a rounded groove into which said stop element resides while being cut, said groove terminating in a reference surface against which said lower end abuts.

28. The kit of claim 24, wherein said cutting block is capable of holding a plurality of stop elements having different diameters, said cutting block having grooves of different sizes to accommodate said different diameters.

29. The kit of claim 24, wherein said cutting block is capable of holding a plurality of stop elements having different lengths, said cutting block having grooves of different sizes to accommodate said different lengths.

30. The kit of claim 24, further including a stop element holder for coupling with said stop element, said stop element holder for forcing said stop element against a reference surface during cutting.

31. A set of stop elements for use with a set of tools that creates bores in living bone, said set of tools including tools having working portions with different dimensions, each of said set of stop elements for use with a particular tool from said set of tools, said tools include a marker on said working portion indicting a distance from a lowermost end, each of said set of stop elements, comprising:
a plastic body for surrounding said tool, said body including a structure for affixing said stop element relative to said tool and an extending portion for fitting over said working portion of said tool, said extending portion including a stop surface positioned at a known position along said working portion of said tool, said stop surface of said stop element being aligned with said marker on said tool; and
wherein said plastic body includes a color marking indicating said particular tool with which said stop element is to be used and an alphanumeric marking indicating a resulting length of said working portion of said particular tool when said stop element is attached thereto.

32. The set of stop elements of claim 31, wherein said set of stop elements includes a plurality of stop elements that are useful on said particular tool and include the same color marking.

33. The set of stop elements of claim 31, wherein said set of stop elements includes a plurality of stop elements useful on each of said set of tools.

34. The set of stop elements of claim 31, wherein said structure includes a plurality of resilient fingers for grasping over a collar of said tool.

35. The set of stop elements of claim 31, wherein said set of stop elements includes a plurality of stop elements for use on at least three different tools.

36. The set of stop elements of claim 31, wherein said stop elements are disposable.

37. The set of stop elements of claim 31, in combination with said set of tools.

38. The combination of claim 35, wherein said set of tools are drill bits.

39. A stop element for use with a tool having a working portion that assists in creating a bore in living bone, comprising:

a generally tubular main body for surrounding said tool, said main body including a connecting portion with a structure for affixing said stop element relative to said tool, wherein said connecting portion includes a plurality of distinct sections, adjacent ones of said plurality of distinct sections are separated by slots for providing flexibility to said connecting portion, said main body further having an extending portion for fitting over said working portion of said tool, said extending portion being positioned at a known position along said working portion of said tool and including a plurality of grooves for severing said extending portion at predetermined lengths.

40. The stop element of claim, wherein said stop element is made of plastic.

* * * * *

UNITED STATES PATENT AND TRADEMARK OFFICE
CERTIFICATE OF CORRECTION

PATENT NO.   : 6,514,258 B1
DATED        : February 4, 2003
INVENTOR(S)  : Brown et al.

It is certified that error appears in the above-identified patent and that said Letters Patent is hereby corrected as shown below:

Title page,
Item [56], OTHER PUBLICATIONS, "Friatec Fritec®-2" reference, delete "Friatec®-2" and insert -- Frialit®-2 --

Column 9,
Line 54, after "an" insert -- extending portion with an --
Line 57, after "end" insert -- of said an extending portion --
Line 58, after "bits" insert -- , wherein said extending portion includes a plurality of grooves for severing said extending portion to reduce its length, a part of said extending portion adjacent to a selected one of said plurality of grooves capable of being said lower end for defining said insertion depth once said extending portion is severed at said selected one of said plurality of grooves --

Column 12,
Line 15, after "claim" insert -- 39 --

Signed and Sealed this

Fifth Day of August, 2003

JAMES E. ROGAN
*Director of the United States Patent and Trademark Office*